United States Patent [19]
Hijiya et al.

[11] Patent Number: 5,763,657
[45] Date of Patent: Jun. 9, 1998

[54] PHOSPHORIC ACID-AMINO ACID-POLYVALENT METAL COMPOSITE SALT AND RUMINANT FEED ADDITIVE COMPOSITION

[75] Inventors: Toyoto Hijiya; Toru Ikeda; Kenichi Mori; Toshihide Yukawa; Tadashi Takemoto; Hajime Kamada, all of Kawasaki, Japan

[73] Assignee: Ajinomoto Co., Inc., Tokyo, Japan

[21] Appl. No.: 894,703

[22] PCT Filed: Nov. 21, 1996

[86] PCT No.: PCT/JP96/03420
§ 371 Date: Aug. 28, 1997
§ 102(e) Date: Aug. 28, 1997

[87] PCT Pub. No.: WO97/24314
PCT Pub. Date: Jul. 10, 1997

[30] Foreign Application Priority Data

Dec. 28, 1995 [JP] Japan .................................. 7-343165
Sep. 5, 1996 [JP] Japan .................................. 8-235309

[51] Int. Cl.$^6$ .............................. C07C 229/00; A23K 1/18
[52] U.S. Cl. ........................ 562/561; 562/553; 562/560; 562/562; 548/339.1; 426/807
[58] Field of Search .......................... 562/11, 553, 560, 562/561, 562; 548/339.1; 426/807

[56] References Cited

U.S. PATENT DOCUMENTS 5,676,966  10/1997  Kitamura et al. .................... 424/438

FOREIGN PATENT DOCUMENTS 59-159741  9/1984  Japan .
96/17822   6/1996  WIPO .

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

The present specification discloses a ruminant feed additive composition which contains as an active ingredient a phosphoric acid-amino acid-polyvalent metal composite salt (final composite salt) which is insoluble in neutral or alkaline water and is soluble in acidic water and which can be obtained by treating a composite salt composed of a basic amino acid, magnesium and phosphoric acid with a salt of a divalent or trivalent (polyvalent) metal other than magnesium, or by treating the above-mentioned composite salt with the polyvalent metal salt and a condensed phosphoric acid component (alone) or the condensed phosphoric acid component and a phosphoric acid component (in combination), this composition taking the form of a powder or granules. The above-mentioned final composite salt can exhibit the excellent stability to neutral or slightly acidic water, namely, the low solubility therein in comparison with the intermediate composite salt, and it can have both the excellent insolubility of the basic amino acid in a rumen of a ruminant and the excellent elution thereof in an abomasum and lower digestive organs.

21 Claims, No Drawings

PHOSPHORIC ACID-AMINO ACID-POLYVALENT METAL COMPOSITE SALT AND RUMINANT FEED ADDITIVE COMPOSITION

TECHNICAL FIELD

The present invention relates to a novel phosphoric acid-amino acid-polyvalent metal composite salt and a ruminant feed additive composition containing the same as an active ingredient. The ruminant feed additive composition of the present invention can be stable in a rumen of a ruminant and release a basic amino acid in an abomasum and lower digestive organs, and it can take the form of a powder or granules.

TECHNICAL BACKGROUND

When biologically active substances such as amino acids, vitamins and the like are orally administered directly into ruminants such as cow, sheep and the like, most of these substances are decomposed with microorganisms in the rumen, and are, therefore, not utilized effectively. Accordingly, rumen by-pass preparations for use in the ruminants by which these biologically active substances are protected from the decomposition with microorganisms in the rumen but are digested and absorbed in the abomasum and lower digestive organs are important in the field of ruminant feed, nutrients, chemicals and the like.

With respect to ruminant feed additives containing a biologically active substance, a method in which a biologically active substance is dispersed in a matrix formed of a hydrophobic substance such as fats and oils or a protective substance such as a basic high-molecular substance, and the dispersion is granulated, or a method in which a core containing a biologically active substance is coated with a hydrophobic substance such as fats and oil or an acid-sensitive substance such as a basic high-molecular substance has been proposed so far.

Concerning the method in which the biologically active substance is dispersed in the protective substance, for example, Japanese Laid-Open Patent Application (Kokai) [hereinafter referred to as "Japanese Kokai"] No. 168,351/1985 proposes a method which comprises mixing a biologically active substance with at least 20% by weight of calcium carbonate and at least 10% by weight of an aliphatic monocarboxylic acid having 14 or more carbon atoms, hardened fats and oils or the like, and pulverizing the mixture. Japanese Patent Publication No. 10,780/1984 proposes a method which comprises dispersing from 30 to 50% by weight of a biologically active substance in a protective substance comprising from 10 to 35% by weight of a salt of an aliphatic monocarboxylic acid having from 14 to 22 carbon atoms or ricinoleic acid and the remainder of an aliphatic monocarboxylic acid having from 14 to 22 carbon atoms, ricinoleic acid or hardened fats and oils.

Concerning the method in which the biologically active substance is coated with the hydrophobic protective substance, for example, Japanese Kokai No. 317,053/1988 proposes a method in which a biologically active substance is coated with a protective agent composed of an aliphatic monocarboxylic acid having from 12 to 24 carbon atoms, hardened fats and oils, lecithin and a glycerin fatty acid ester.

Concerning the method in which the biologically active substance is coated with the acid-sensitive protective substance, for example, Japanese Kokai No. 46,823/1979 proposes a method in which a biologically active substance is coated with a coating composition containing a film-forming basic high-molecular substance. Japanese Kokai No. 217,625/1992 proposes a method in which a biologically active substance is spray-coated with casein in the form of an aqueous emulsion or an aqueous dispersion.

However, in the method in which the biologically active substance is dispersed into the protective substance and the dispersion is pulverized, the biologically active substance is present near surfaces of particles obtained. Accordingly, when the protection is taken seriously, the content of the biologically active substance has to be notably decreased. Since the residence time of the water-soluble biologically active substance in the rumen is between 10-odd hours and several days, this biologically active substance can hardly be protected sufficiently.

Further, a method in which a biologically active substance-containing core is coated with an acid-sensitive high-molecular substance or a hydrophobic protective substance has been also proposed. However, in view of production of a formula feed which has been increasingly conducted in recent years, the thus-obtained coated particles of the feed additive composition undergo mechanical granulation and/or coating destruction owing to mixing or pulverization with a starting material of a formula feed such as another feed composition, and a stability in a rumen of a ruminant is impaired in many cases. Thus, the composition is not said to be a multi-purpose feed additive composition.

Thus, it is advisable that a feed additive which can withstand mixing or pulverization with another feed composition take itself the form of a powder or granules (preferably uniform granules) and prevent release of a biologically active substance in the rumen but allow elution of the biologically active substance in the abomasum and lower digestive organs. However, when the basic amino acid is used to improve nutrition of the feed, a substance which is composed of a basic amino-acid-containing composition and which takes the form of a powder or (uniform) granules that are neutral, insoluble and acid-soluble is only phosphorus wolframate.

Japanese Kokai No. 98,357/1988 discloses a ruminant feed additive composition in which a salt of a basic amino acid and an acidic phosphate is coated with a synthetic polymer. Among various salts in this document, the salt of the acidic phosphoric acid alkaline-earth metal salt and the basic amino acid corresponds to an analogue of a precursor composite salt (which is sometimes referred to as "an intermediate composite salt" in the present specification) of a phosphoric acid-amino acid-polyvalent metal composite salt (which is sometimes referred to as "a final composite salt" in the present specification) in the present invention. However, the salt of the acidic phosphoric acid alkaline-earth-metal salt and the basic amino acid in this document has the composition that the molar ratio of phosphoric acid, alkaline-earth metal and basic amino acid is 1:0.5:1 to 2 which is different from that of the precursor composite salt composed of phosphoric acid, alkaline-earth metal (specifically, magnesium) and basic amino acid in the present invention. The salt of the acidic phosphoric acid alkaline-earth-metal salt and the basic amino acid in the present invention is decomposed in water over the course of time to form an alkaline-earth-metal secondary phosphate, a basic amino-acid primary phosphate or a basic amino-acid secondary phosphate. Since the basic amino-acid phosphate exhibits quite a high water-solubility, this salt is substantially neutral and water-soluble in view of the solubility of the basic amino acid.

Phosphoric acid is formed into various salts with alkaline-earth metals, and some of them are insoluble in neutral or alkaline water and are soluble in acidic water. For example, it is known that calcium secondary phosphate, magnesium tertiary phosphate and the like are accumulated as scales in an equipment of fermentation industrial plants in which phosphoric acid is often used, causing troubles in the equipment. Ammonium magnesium phosphate shows the similar nature. With respect to a composite salt (tertiary phosphoric acid salt) comprising 1 mol of phosphoric acid, 1 mol of an alkaline-earth metal and 1 mol of a basic amino acid in which an ammonium ion is replaced with an equivalent basic amino acid as a basic ion, and a tertiary phosphoric acid salt and/or a secondary phosphoric acid salt comprising 1 mol of phosphoric acid, from 1 to 1.45 mols of an alkaline-earth metal and from 0.05 to 1 mol of a basic amino acid, only a composite salt disclosed in a prior application [Japanese Patent Application No. 306,385/1994, WO 96/17822 (13 Jun. 1996)] of the present inventors is known.

It is a composite salt represented by the following formula (a) or (b), among composite salts (intermediate composite salts) described in WO 96/17822, that corresponds to the phosphoric acid-amino acid-polyvalent metal composite salt of the present invention by improving the solubility thereof.

  (a)

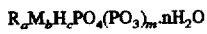  (b)

wherein R represents a basic amino acid, M represents an alkaline-earth metal, and H represents hydrogen.

DISCLOSURE OF THE INVENTION

Under the above-mentioned circumstances, the present invention aims to provide, in view of a safety and economics, a compound which contains a basic amino acid, and which is not dissolved in a rumen of a ruminant but allows elution of a basic amino acid in an abomasum and lower digestive organs and absorption and digestion of the same therein at good efficiency, and a composition containing the same which composition takes the form of a powder or (uniform) granules.

They found before that various composite salts comprising a basic amino acid, an alkaline-earth metal and phosphoric acid are insoluble in neutral or alkaline water and is soluble in acidic water, and take the form of a powder (Japanese Patent Application No. 306,385/1994). They have assiduously conducted investigations to achieve the above object, and have consequently found that a composite salt which can be obtained by treating, among the above-mentioned various composite salts, a composite salt comprising a basic amino acid, magnesium and orthophosphoric acid with (i) another divalent or trivalent (polyvalent) metal in combination with (ii) condensed phosphoric acid and/or orthophosphoric acid exhibits a better stability to neutral or slightly acidic water, namely a lower solubility therein, and that it exhibits an excellent insolubility in the rumen of the ruminant and an excellent elution property in the abomasum and lower digestive organs. These findings have led to the completion of the present invention.

That is, the present invention relates to a phosphoric acid-amino acid-polyvalent metal composite salt represented by the following formula (1) or (2), which comprises a basic amino acid, magnesium and a polyvalent metal other than magnesium and phosphoric acid, and which is insoluble in neutral or alkaline water and is soluble in acidic water, a process for producing the same, and a ruminant feed additive composition containing the above-mentioned composite salt.

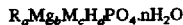  (1)

wherein

R represents a basic amino-acid hydrogen cation,

Mg represents magnesium,

M represents a polyvalent metal of m-valence other than magnesium in which m is 2 or 3, H represents hydrogen, a is between 0.05 and 1.0, b is between 0.85 and 1.43, c is between 0.02 and 0.6, d is between 0 and 0.3, a+b×2+c×m+d=3, and n is between 0 and 20.

  (2)

wherein

R represents a basic amino-acid hydrogen cation,

Mg represents magnesium,

M represents a polyvalent metal of q-valence other than magnesium in which q is 2 or 3, H represents hydrogen, a is between 0.05 and 0.4, b is between 0.90 and 1.47, c is between 0.01 and 1.4, d is between 0 and 0.3, a+2×b+q×c+d=m+3, m is 0<m<1.12, and n is between 0 and 10.

The present invention is described in detail below.

First of all, the phosphoric acid-amino acid-polyvalent metal composite salt of formula (1) is described.

Orthophosphoric acid which is starting phosphoric acid in producing the composite salt of the present invention can be used in the form of a free acid or salt, and in the form of an aqueous solution having an appropriate concentration.

The starting basic amino acid which is used in producing the composite salt includes natural basic amino acids such as lysine, arginine and ornithine; basic derivatives thereof; and basic derivatives of neutral amino acids. These amino acids are used either singly or in combination. Specific examples thereof include natural basic amino acids such as lysine, arginine and ornithine; basic derivatives such as basic amino-acid-containing peptides; and basic derivatives of neutral amino acids, for example, amides and esters of amino acids such as methionine, tryptophane and threonine.

Examples of the divalent or trivalent (polyvalent) metal other than magnesium which constitutes the composite salt in the present invention include alkaline-earth metals such as calcium, strontium and barium; transition metals such as aluminum, iron, cobalt, manganese and chromium; and other divalent metals such as zinc and cadmium. Of these, salts of calcium, aluminum, iron and zinc are preferable because the composite salt is received biologically safely. In the production of the composite salt in the present invention, these metals can be obtained in the form of appropriate salts.

The phosphoric acid-amino acid-polyvalent metal composite salt of formula (1) in the present invention is a composite salt which can be obtained by first causing, for example, a basic amino acid, a magnesium salt and phosphoric acid to exist in an aqueous solution under neutral or alkaline conditions in which the basic amino acid is used at a relatively high concentration to obtain a crystalline precipitate (intermediate composite salt which is represented by, for example, formula (4) to be described later), and then treating the same with a divalent or trivalent (polyvalent) metal other than magnesium. A specific example thereof is a salt corresponding to a mixture containing a tertiary phosphate of orthophosphoric acid as a main component and a secondary phosphate in which the amount of phosphoric acid is 1 mol, that of the basic amino acid is between 0.05 and 1 mol (a), that of magnesium is between 0.85 and 1.43 mols (b), that of the divalent or trivalent (polyvalent) metal of polyvalence (m) other than magnesium is between 0.02 and 0.6 mols (c), that of the residual hydrogen (d) of phosphoric acid is between 0 and 0.3 mols (d), a+2b+mc+d=3, that of the secondary phosphate is ½ or less of that of the tertiary phosphate (molar ratio), and a water content in the composite salt is 30% or less. $H_2O$ is theoretically 0, 1 or 2, but it is between 0 and 20 depending on the dry condition.

A process for producing the phosphoric acid-amino acid-polyvalent metal composite salt in the present invention is not particularly limited so long as the resulting composite salt is insoluble in a neutral or alkaline aqueous solution and is soluble in an acidic aqueous solution. Preferable is a process in which the intermediate composite salt is mixed with a solution of a salt of a divalent or trivalent (polyvalent) metal other than magnesium, and the mixture is separated and dried. And preferable is a process in which the intermediate composite salt is mixed with a solution of a salt of a divalent or trivalent(polyvalent) metal other than magnesium and with orthophosphoric acid and/or orthophosphoric acid salt solution, and the mixture is separated and dried.

The process for producing the intermediate composite salt is preferably grouped into the following four.

In the first process, a secondary phosphate of magnesium is dispersed into a large amount of an aqueous solution of a basic amino acid (the aqueous solution of the basic amino acid is basic), the dispersion is heated, and the resulting precipitate is separated and as required, is washed. Specifically, magnesium hydrogenphosphate is added to a large amount of a concentrated aqueous solution (basic) of a free basic amino acid formed by dehydrochlorination through treatment with an ion-exchange resin from a basic amino-acid salt, for example, lysine hydrochloride, and the mixture is heat-stirred. Magnesium hydrogenphosphate in the mixed solution disappears over the course of time, and the phosphoric acid-amino acid-magnesium composite salt is formed as a precipitate. The precipitate is subjected to solid-liquid separation, and the resulting solid phase is washed with water as required to remove the excess basic amino acid. The residue is dried to obtain a desired intermediate composite salt. In the composition of this intermediate composite salt, for example, the molar ratio of phosphoric acid, basic amino acid and magnesium is 1:0.8 to 1.0:1.1.

In the second process, an aqueous solution of a magnesium salt and orthophosphoric acid are mixed in a large amount of an aqueous solution of a basic amino acid (this aqueous solution is basic), the resulting precipitate is separated, and the precipitate separated is washed as required. Specifically, 3 mols or more of a concentrated aqueous solution of a basic amino acid are neutralized with 1 mol of orthophosphoric acid to form a tertiary phosphate solution of a high concentration. Then, from 1.0 to 1.45 mols of a concentrated aqueous solution of a magnesium neutral salt such as magnesium chloride and/or magnesium sulfate are added thereto, and the mixture is stirred. The resulting precipitate is subjected to solid-liquid separation. The excess basic amino acid is washed with water, and the residue is dried to form the desired intermediate composite salt.

In the third process, a primary phosphate solution of a basic amino acid is mixed with magnesium hydroxide and/or magnesium oxide, the resulting precipitate is separated, and the precipitate separated is washed as required. Specifically, from 0.7 to 1.4 mols of a concentrated aqueous solution of a basic amino acid is mixed and neutralized with 1.0 mol of orthophosphoric acid. The concentrated aqueous solution of the basic amino acid primary phosphate is mixed with an aqueous dispersion of from 1.0 to 1.45 mols of magnesium hydroxide and/or magnesium oxide. The resulting precipitate is separated. The excess basic amino acid is washed with water as required, and the precipitate separated is then dried to form a desired intermediate composite salt. In the composition of this intermediate basic amino acid, for example, the molar ratio of phosphoric acid, basic amino acid and magnesium is 1:0.5 to 0.8:1.0 to 1.45.

In the fourth process, phosphoric acid, an aqueous solution of a basic amino acid and magnesium hydroxide and/or magnesium oxide are mixed, and the mixture is then heat-dried. For example, the aqueous solution of the basic amino acid is mixed and neutralized with orthophosphoric acid at a molar ratio of 0.05 to 0.8:1.0. To this solution are then added from 1.0 to 1.45 mols of magnesium hydroxide and/or magnesium oxide, and the mixture is heat-dried. Further, from 0.05 to 0.8 mols of a concentrated aqueous solution of a basic amino acid is mixed and neutralized with 1.0 mol of orthophosphoric acid to form a concentrated mixed aqueous solution of a primary phosphate of a basic amino acid and orthophosphoric acid. To this solution are added from 1.0 to 1.45 mols of magnesium hydroxide and/or magnesium oxide in the form of an aqueous dispersion. The resulting precipitate containing the reaction mixture is directly dried through heating or the like to give a desired intermediate composite salt.

In these four processes, the concentrated aqueous solution (which is basic as mentioned above) of the basic amino acid is adopted as a starting material, and the amino-acid composite salt (intermediate composite salt) is formed by the reaction in which the basic amino acid is used at a relatively high concentration. In the present invention, the concentration of the basic amino acid is preferably between 10 and 60 parts by weight per 100 parts by weight of the total water content present in the reaction system in the case of the second process in which the highest concentration is selected, and it is preferably between 3 and 20 parts by weight per 100 parts by weight of the total water content present in the reaction system in the case of the fourth process in which the lowest concentration is selected.

These four processes can also be used in combination as required. Specific examples thereof include a process in which an appropriate amount of a concentrated aqueous solution of a neutral salt of orthophosphoric acid and/or magnesium is added to a reaction solution in which the magnesium phosphate-amino acid composite salt is formed as a precipitate in the first process, these are mixed while being stirred, and the mixture is heated, whereby the concentrated aqueous solution is reacted with the large amount of the basic amino acid remaining in the reaction solution; and a process in which an appropriate amount of magnesium hydroxide is added to a reaction solution in which a magnesium phosphate-amino acid composite salt is formed as a precipitate in the second process, whereby magnesium hydroxide is reacted with large amounts of the basic amino acid and phosphoric acid remaining in the reaction solution.

In the present invention, the salts of the divalent or trivalent (polyvalent) metals other than magnesium which are used when treating the intermediate composite salt are not particularly limited. That is, the polyvalent metal salts can be used in the solid state either singly or in combination as solid mixed salts. Needless-to-say, the salts can be used in the form of a solution or a dispersion. Preferable is a weakly acidic or basic aqueous solution or dispersion containing at least 0.001 parts by weight, per 100 parts by weight of the solution, of the polyvalent metal ion other than magnesium. Specific examples thereof include aqueous solutions of aluminum salts such as aluminum chloride, polyaluminum chloride, ammonium sulfate, ammonium alum and potassium alum; aqueous solutions or aqueous dispersions of calcium salts such as calcium chloride, calcium sulfate, calcium hydroxide and calcium nitrate; aqueous solutions of iron salts such as ferrous chloride, ferric chloride, ferrous sulfate, ferric sulfate, potassium iron sulfate and ammonium iron sulfate; and aqueous solutions or aqueous dispersions of zinc salts such as zinc chloride, ammonium zinc chloride and zinc hydroxide. These solutions (or dispersions) of the polyvalent metals other than magnesium may be used either singly or in combination as a mixed salt solution (or dispersion) or a composite salt solution (or dispersion).

The necessary amount of the divalent or trivalent (polyvalent) metal salt other than magnesium, which is used to treat the intermediate composite salt in the present invention varies depending on the time of the contact with the intermediate composite salt, the concentration of the solution or the dispersion of the divalent or trivalent (polyvalent) metal salt other than magnesium and the dispersion concentration of the intermediate composite salt in the contact. However, since most of the divalent or trivalent (polyvalent) metal ions other than magnesium migrate into the desired composite salt, the concentration of this metal salt is preferably between 0.02 and 0.6 mols per mol of phosphoric acid in the intermediate composite salt.

In this invention, when the intermediate composite salt is treated with the divalent or trivalent (polyvalent) metal salt other than magnesium, a method in which the intermediate composite salt is prepared previously, then mixed with a salt solution of a divalent or trivalent (polyvalent) metal other than magnesium, separated and dried is preferably employed. At this time, the intermediate composite salt is dried previously and is used in the form of a powder. Also available are a method in which an undried intermediate composite salt is dispersed into a salt solution of a divalent or trivalent (polyvalent) metal other than magnesium, and the dispersion is then separated and dried, and a method in which an undried intermediate composite salt is mixed with, for example, calcium hydroxide in the form of a powder or an aqueous dispersion, and the mixture is dried as it is.

In the present invention, the treatment of the intermediate composite salt with the salt of the divalent or trivalent (polyvalent) metal other than magnesium is effective for further increasing the insoluble/soluble-property of the intermediate composite salt which is insoluble in neutral or alkaline water and is soluble in acidic water and for exhibiting the insolubility in a neutral buffer aqueous solution too. This is presumably because when the intermediate composite salt is treated with the salt of the divalent or trivalent (polyvalent) metal other than magnesium, a surface layer which is formed of orthophosphoric acid and the salt of the divalent or trivalent (polyvalent) metal other than magnesium and which is more insoluble is formed on the surface of the intermediate composite salt so as to form a final composite salt which is insoluble in a neutral buffer aqueous solution and is soluble in an acidic buffer aqueous solution.

And preferable is a process in which the intermediate composite salt is mixed with a solution of a salt of a divalent or trivalent(polyvalent) metal other than magnesium and with orthophosphoric acid and/or orthophosphoric acid salt solution, and the mixture is separated and dried.

Next, the phosphoric acid-amino acid-polyvalent metal composite salt of formula (2) is described.

The composite salt of formula (2) in the present invention can be produced by bringing a phosphoric acid-amino acid-magnesium composite salt (intermediate composite salt) represented by formula (4)

 (4)

wherein

R represents a basic amino-acid hydrogen cation,

Mg represents magnesium,

H represents hydrogen, a is between 0.05 and 1.0, b is between 1.0 and 1.47, c is between 0 and 0.3, a+2×b+c=3, and n is between 0 and 10 into contact with a condensed phosphoric acid component and a substance of a divalent or trivalent (polyvalent) metal other than magnesium in an aqueous medium.

Specific examples of the substance of the divalent or trivalent (polyvalent) metal other than magnesium include aluminum salts such as aluminum chloride, polyaluminum chloride, aluminum sulfate, ammonium alum and potassium alum; calcium salts or hydroxides such as calcium chloride, calcium sulfate, calcium hydroxide and calcium nitrate; iron salts such as ferrous chloride, ferric chloride, ferrous sulfate, ferric sulfate, potassium iron sulfate and ammonium iron sulfate; and zinc salts such as zinc chloride and ammonium zinc chloride; and zinc hydroxide. These polyvalent metal salts may be used either singly or in combination, and a solid mixed salt, a solution or a composite salt solution thereof are also available.

Examples of the condensed phosphoric acid component which is used in treating the Mg salt in the present invention include polyphosphoric acids such as pyrophosphoric acid, tripolyphosphoric acid, tetrapolyphosphoric acid and the like; metaphosphoric acids such as trimetaphosphoric acid, tetrametaphosphoric acid, hexametaphosphoric acid and the like; and salts thereof. Orthophosphoric acid component; including orthophosphoric acid and a salt thereof, can be used with the condensed phosphoric acid component. Examples of the salts include salts of metals such as sodium, potassium, magnesium, calcium, iron, zinc and aluminum; and an ammonium salt. Especially when the divalent or trivalent metal salts such as a calcium salt and an iron salt are used, the above-mentioned polyvalent metal substance is contained at the same time, making it possible to decrease the amount of the polyvalent metal substance. These condensed phosphoric acid component (and the orthophosphoric acid component which is used as required) can be used either singly or in combination. These components can be used in their own forms regardless of the solid state or the liquid state. They can also be used in the form of an aqueous solution.

The necessary amounts of the divalent or trivalent (polyvalent) metal substance and the condensed phosphoric acid component (and the orthophosphoric acid component which is used as required) which are used when treating the Mg salt in the present invention have to be determined in consideration of the following two points. That is, the amounts vary depending on the time of the contact with the Mg salt and the dispersion concentration of the Mg salt in the contact. However, almost all of the polyvalent metal ions from the polyvalent metal substance and the condensed phosphoric acid component (and the orthophosphoric acid component which is used as required) migrate into the desired final composite salt. Further, in general, when the amounts of the polyvalent metal substance and the condensed phosphoric acid component (and the orthophosphoric acid component which is used as required) are increased, the solubility of the final composite salt is suppressed, but the content of the basic amino acid which is required as a feed is decreased. Accordingly, in order to develop the effect given by the decrease in the solubility and maintain the content of the basic amino acid, both of the above-mentioned components can be used at amounts of from 0.004 to 1.2, preferably from 0.01 to 0.5 per mol of phosphoric acid of the Mg salt.

The Mg salt (intermediate composite salt), the polyvalent metal substance and the condensed phosphoric acid component (and the orthophosphoric acid component which is used as required) are usually brought into contact with one another in an aqueous medium. In general, the Mg salt, the polyvalent metal substance and the condensed phosphoric acid component (and the orthophosphoric acid component which is used as required) are mixed in an aqueous solution while being stirred.

The Mg salt (intermediate composite salt) used herein can be formed by, for example, reacting orthophosphoric acid and magnesium hydroxide with a basic amino acid, isolating the salt from the reaction solution, and drying the same. However, the isolation is not necessarily conducted, and the reaction solution itself may be treated with the condensed phosphoric acid component (and the orthophosphoric acid component which is used as required) and the divalent or trivalent (polyvalent) metal substance. The wet crystals of the Mg salt which are obtained through solid-liquid separation are not necessarily dried. The desired polyvalent metal composite salt (final composite salt) can be formed also by kneading the wet crystals of the Mg salt with the polyvalent metal substance and the condensed phosphoric acid component (and the orthophosphoric acid component which is used as required).

In the mixing procedure for contact of these three components, it is important that the procedure is always conducted under neutral or alkaline conditions. That is, the Mg salt which is one of the starting materials and the desired polyvalent metal composite salt are stable under neutral or alkaline conditions but are relatively unstable under acidic condition and tend to be decomposed and dissolved in this condition. For example, when polyphosphoric acid is used as the condensed phosphoric acid component and calcium hydroxide as the polyvalent metal substance, it is better to add calcium hydroxide and polyphosphoric acid in this order to a slurry containing the Mg salt than to add the Mg salt to an aqueous solution of polyphosphoric acid (acidic) and then add calcium hydroxide (alkaline). It is also recommendable to add polyphosphoric acid and calcium hydroxide at the same time while maintaining the pH of the slurry containing the Mg salt at least 6, preferably at least 7. However, when the time is short, exposure to acidic conditions does not give so great an adverse effect.

When a substance having a relatively low solubility, such as calcium hydroxide, is used as the polyvalent metal substance, it is sometimes incorporated in an unreacted state into the desired polyvalent metal composite salt (final composite salt) under some reaction conditions. However, the influence of it on the stability in the rumen and on the solubility in the abomasum and lower digestive organs is not particularly problematic.

The temperature at which these three components are mixed for the contact thereof is not particularly limited. The mixing can be conducted at a temperature of from 0° to 80° C. The concentration of the reaction mixture in the mixing is not particularly limited so long as the uniform mixing is conducted. It is usually between 5 and 40% by weight as an Mg salt.

After the mixing of the three components is completed, the mixture can be subjected at once to solid-liquid separation. In order to complete the reaction, it is preferable that the mixture be stirred for from 30 minutes to 1 day. After the completion of the contact (mixing) procedure, the mixture is subjected to solid-liquid separation such as filtration, shaking-separation or the like. The wet crystals of the polyvalent metal salt obtained have usually a water content of from 40 to 80%. When the wet crystals are dried, the water content usually becomes between 0 and 15%, though it varies depending on the drying conditions.

In the present invention, the treatment of the Mg salt with the condensed phosphoric acid component (and the orthophosphoric acid component which is used as required) and the substance of the divalent or trivalent (polyvalent) metal other than magnesium is effective for further increasing the soluble-property of the Mg salt which is insoluble in neutral or alkaline water and is soluble in acidic water and for exhibiting the insolubility in a neutral buffer aqueous solution too. This is presumably because when the Mg salt is treated with the substance of the polyvalent metal other than magnesium and the condensed phosphoric acid component (and/or the orthophosphoric acid component which is used as requied), an insoluble surface layer which is made of condensed phosphoric acid (and/or orthophosphoric acid which is used as requied) and the polyvalent metal salt is formed on the surface of the Mg salt, and a part of the polyvalent metal cation is replaced with the basic amino-acid hydrogen cation of the Mg salt to crosslink the Mg salt and the condensed phosphoric acid component (and/or the orthophosphoric acid component which is used as required) of the surface layer portion. As a result, a desired final composite salt which is insoluble in a neutral buffer aqueous solution and is soluble in an acidic buffer aqueous solution is formed.

The compound of formula (3) is a phosphoric acid-amino acid-polyvalent metal composite salt, among those represented by formula (2), wherein the polyvalent metal other than magnesium is a polyvalent metal other than an alkaline-earth metal.

  (3)

wherein

R represents a basic amino-acid hydrogen cation,

Mg represents magnesium,

Z represents a polyvalent metal of q-valence other than an alkaline-earth metal in which q is 2 or 3, H represents hydrogen, a is between 0.05 and 0.4, b is between 0.90 and 1.47, c is between 0.01 and 1.4, d is between 0 and 0.3, a+2×b+q×c+d=m+3, m is 0<m<1.12, and n is between 0 and 10.

The phosphoric acid-amino acid-polyvalent metal composite salt (final composite salt) of formula (1) or (2) in the present invention has a remarkable improved soluble-property that it is insoluble in neutral or alkaline water and is soluble in acidic water. Accordingly, it is stable in a neutral rumen, and is completely dissolved in an acidic abomasum to release the basic amino acid, and the basic amino acid released is absorbed in the small intestine. That is, the composite salt can be used as a ruminant feed additive composition in the form of a powder in which the basic amino acid that is the (active) ingredient is protected from the decomposition with microorganisms in the rumen quite effectively, and is digested and absorbed in the abomasum and lower digestive organs.

This composite salt can be used as a ruminant feed additive composition in the form of a powder. Besides, it can be used by forming the same into granules having an appropriate diameter.

In the present invention, the granules of the phosphoric acid-amino acid composite salt are especially preferably uniform granules. With respect to the uniform granules in the present invention, when the granules are destroyed to form granular materials having a diameter of from approximately 1 to 2 mm, the composition thereof is unchanged. That is, the limit of the diameter in which granules are destroyed through chewing is between approximately 1 and 2 mm. Therefore, when the composition of the granular materials having a diameter of from approximately 1 to 2 mm is unchanged, the composition of the granular materials after chewing is fixed. Thus, when the granules are mixed or pulverized with the other feed components, the elution of the basic amino-acid component is not greatly changed. Thus, it is preferable.

The granulation can be conducted by a usual method so long as the above-mentioned uniformity is provided. Preferable are a method in which the composite salt is mixed with an appropriate binder, and the mixture is granulated through extrusion-granulation, rolling-granulation, compression-granulation, melt-spray-granulation or the like, a method in which a slurry is spray-dried, and a method in which a powder is granulated together with an appropriate binder through granulation using a fluidized bed or through stirring-granulation.

The binder is not particularly limited, and an ordinary binder can be used. The binder includes water-soluble binders and hydrophobic binders. Specific examples of the water-soluble binders include water-soluble polysaccharides such as a starch, a carboxymethyl cellulose salt, an alginate, hydroxypropyl cellulose and a starch glycolic acid salt; water-soluble proteins such as casein sodium, gelatin and soybean protein; saccharides such as molasses, lactose and dextrin; and synthetic high-molecular substances such as a polymethacrylate salt, polyvinyl alcohol and polyvinyl pyrrolidone. Specific examples of the hydrophobic binders include natural waxes such as a shellac resin, a rosin, a bees wax and a paraffin wax; higher aliphatic acids such as cetanol and stearic acid; materials associated with fats and oils, such as higher fatty acid metal salts, animal and vegetable fats and oils, and hardened animal and vegetable fats and oils; nonionic surfactants such as glycerin monostearate; and semi-synthetic resins and synthetic high-molecular substances such as acetyl cellulose, polyvinyl acetate, ester gum and a coumarone resin.

The ratio of the binder to the phosphoric acid-amino acid-polyvalent metal composite salt in the granulation varies depending on the type of the binder. The binder in an amount of from 0.1 to 50% by weight per 100 parts by weight of the composite salt achieves the predetermined object and is sufficient for shape retention. Further, the diameter of the granules is not particularly limited so long as it is appropriate for intake of a ruminant. The granules having an average diameter of approximately 5 mm or less is preferable because the irregularity of the feed is decreased. The granules having an average diameter of from 2 to 0.2 mm are especially preferable because they facilitate the mixing with other feed components.

The granules containing the phosphoric acid-amino acid-polyvalent metal composite salt in the present invention can be prepared by adding, besides the composite salt and the binder, other additives in order to adjust the specific gravity, to increase the strength of granules, to increase the melt-destruction in the abomasum, to improve processability in preparation of the granules, and so forth. The additives are selected from powders and waxes to form uniform granules. Specific examples thereof include inorganic substances such as carbonates, phosphates and hydroxides of alkaline-earth metals, talc, bentonite, clay and fine silica; and organic substances such as paraffin wax, polyethylene powder, pulp powder, cellulose powder and xanthone.

In addition, the granules containing the phosphoric acid-amino acid composite salt in the present invention can be prepared by uniformly dispersing the other biologically active substance unless impairing the protection of the composite salt in the rumen and the elution thereof in the abomasum. The other biologically active substance includes known nutrients and chemicals such as amino acids, derivatives thereof, hydroxy compounds of amino acids, vitamins and veterinary agents. These may be used either singly or in combination.

Specific examples thereof include amino acids such as methionine, tryptophan and threonine; amino-acid derivatives such as calcium salts of N-acylamino acid and N-hydroxymethyl methionine; amino-acid hydroxy compounds such as 2-hydroxy-4-methylmercaptobutyric acid and its salt; calory sources such as starch, fatty acid and fatty acid metal salt; vitamins such as vitamin A, vitamin A acetate, vitamin A palmitate, vitamin B group, thiamine, thiamine hydrochloride, riboflavin, nicotinic acid, nicotinic acid amide, calcium panthotenate, choline panthotenate, pyridoxine hydrochloride, choline chloride, cyanocobalamin, biotin, folic acid, p-aminobenzoic acid, vitamin $D_2$, vitamin $D_3$ and vitamin E, as well as substances having the similar properties; tetracycline-type, amino-macrolide-type, macrolide-type and polyether-type antibiotics; insect repellents such as negphon; vermifuges such as piperadine; and hormones such as estrogen, stilbestrol, hexestrol, thyroprotein, goitrogen and growth hormone.

BEST MODE OF CARRYING OUT THE INVENTION

The present invention is illustrated more specifically by referring to the following Examples and Comparative Examples. However, the present invention is not limited thereto.

With respect to a biologically active substance in tests and Examples, an amount of an amino acid and an amount of an amino acid eluted were measured through liquid chromatography.

Further, the contents of phosphorus and metal components were measured through ICP (induction binding plasma) emission spectral analysis and a dry weight decrease method (135° C., 30 minutes) respectively.

The tests for the elution and the protection of a basic amino acid were conducted by the following methods (a) to (d) with respect to Examples 1 to 15 and by the following methods (e) to (g) with respect to Examples 16 to 28.

(a) Elution into pure water

One gram of the sample prepared was charged into a 200-milliliter Erlenmeyer flask, and 100 ml of pure water were poured therein. The solution was sonicated at room temperature for 10 minutes, and was filtered. Subsequently, the amount of a basic amino acid in the filtrate (amount of elution from the sample) was analyzed, and the elution into pure water was evaluated in terms of a rate of elution.

The rate of elution was calculated using the following equation (i).

Rate of elution (=elution) (%)=$A/B$×100 (%)     (i)

A: amount of a basic amino acid eluted

B: amount of a basic amino acid in a sample used (b) Protection in a corresponding rumen solution Approximately 0.5 g of the sample prepared were charged into a 300-milliliter Erlenmeyer flask, and 200 ml of a McDougall buffer solution corresponding to a rumen solution was poured therein. The mixed solution was shaken at 39° C. for 24 hours. After the completion of the shaking, the solution was filtered. The amount of a basic amino acid in the filtrate (amount of elution from the sample) was analyzed, and protection in the corresponding rumen solution was calculated using the following equation.

Protection (%)=[($B$–$A$)/$B$]×100 (%)     (ii)

wherein A and B are the same as in equation (i).

(c) Protection in a corresponding rumen solution in the administration of a small amount of a sample In order to evaluate a bypass property depending on the amount of the sample in the rumen, approximately 0.2 g of the sample prepared were charged into a 300-milliliter Erlenmeyer flask, and 200 ml of a McDougall buffer solution corresponding to the rumen solution were poured therein. The mixed solution was shaken at 39° C. for 24 hours. After the completion of the shaking, the solution was filtered. The amount of a basic amino acid in the filtrate (amount of elution from the sample) was analyzed, and the protection in the corresponding rumen solution in the administration of the small amount of the sample was calculated using the above-mentioned equation (ii).

McDougall buffer solution

Buffer solution obtained by dissolving the following reagents into 1,000 ml of water

| | |
|---|---|
| sodium hydrogencarbonate: | 7.43 g |
| disodium hydrogenphosphate 12-hydrate: | 7.00 g |
| sodium chloride: | 0.34 g |
| potassium chloride: | 0.43 g |
| magnesium chloride 6-hydrate: | 0.10 g |
| calcium chloride: | 0.05 g |

(d) Elution into a corresponding abomasum solution

Approximately 0.5 g of the sample prepared were charged into a 300-milliliter Erlenmeyer flask, and 200 ml of an acetate-phosphate buffer solution corresponding to a rumen solution was poured therein. The mixed solution was shaken at 39° C. for 1 hour. After the completion of the shaking, the solution was filtered. The amount of a basic amino acid in the filtrate (amount of elution from the sample) was analyzed, and the elution into the corresponding abomasum solution was calculated using the above-mentioned equation.

Acetate-phosphate buffer solution

Buffer solution prepared by dissolving the following reagents into 1,000 ml of water and adjusting the pH of the solution to 2.2 with hydrochloric acid.

| | |
|---|---|
| sodium dihydrogenphosphate 2-hydrate | 1.95 g |
| sodium acetate 3-hydrate | 3.40 g |

(e) Elution into pure water

One gram of the sample prepared was charged into a 50-milliliter messflask, and 50 ml of pure water were poured therein. The solution was sonicated at room temperature for 10 minutes, and was filtered. The amount of a basic amino acid eluted in the filtrate was analyzed, and the elution into pure water was calculated using the above-mentioned equation (i).

(f) Protection in a corresponding rumen solution

Approximately 0.1 g of the sample prepared were charged into a 50-milliliter Erlenmeyer flask, and 20 ml of a 0.5-M phosphate buffer solution (pH 6.0) corresponding to a rumen solution was poured therein. The mixed solution was shaken at 25° C. for 20 minutes. After the completion of the shaking, the solution was filtered. The amount of a basic amino acid eluted in the filtrate was analyzed, and the protection in the corresponding rumen solution was calculated using the above-mentioned equation (ii).

(g) Elution into a corresponding abomasum solution

Approximately 0.25 g of the sample prepared were charged into a 300-milliliter Erlenmeyer flask, and 50 ml of an acetate-phosphate buffer solution corresponding to an abomasum solution was poured therein. The mixed solution was shaken at 39° C. for 2 hours. After the completion of the shaking, the solution was filtered. The amount of a basic amino acid eluted in the filtrate was analyzed, and the elution into the corresponding abomasum solution was calculated using the above-mentioned equation (i).

Acetate-phosphate buffer solution

Buffer solution prepared by dissolving the following reagents into 1,000 ml of water and adjusting the pH of the solution to 2.2 with hydrochloric acid.

| | |
|---|---|
| sodium dihydrogenphosphate 2-hydrate | 3.55 g |
| dipotassium hydrogenphosphate | 1.67 g |
| acetic acid | 3.90 g |

EXAMPLE 1

Intermediate composite salt of formula (4) [1]

Magnesium secondary phosphate 3-hydrate (174.3 g) was added to 1,300 g of an L-lysine aqueous solution (concentration: 45% by weight), and the mixture was heat-stirred at 80° C. for 3 hours. Consequently, particulate crystals of magnesium secondary phosphate disappeared, and fine crystals were formed in large amounts. The resulting crystals were filtered, washed with 1,000 ml of water, and then dried at 60° C. under reduced pressure to obtain 285 g of a white crystalline powder.

One gram of this white powder was added to 100 ml of each of pure water and the corresponding rumen solution, and the mixture was stirred. As a result, no apparent change in the form of the sample was observed in either case. This product was designated an intermediate composite salt I.

EXAMPLE 2

Intermediate composite salt of formula (4) [2]

An L-lysine aqueous solution (4,386 g, concentration: 20% by weight) was mixed and neutralized with 231 g of phosphoric acid (concentration: 85%). To this solution was added a solution of 493 g of magnesium sulfate 7-hydrate in 1,000 ml of water at a time. The resulting gel-like precipitate was filtered, washed with 12,000 ml of water, and dried at 60° C. under reduced pressure to obtain 280 g of a white powder.

One gram of this white powder was added to 100 ml of each of pure water and the corresponding rumen solution, and the mixture was stirred. As a result, no apparent change in the form of the sample was observed in either case. This product was designated an intermediate composite salt II.

EXAMPLE 3

Intermediate composite salt of formula (4) [3]

An L-lysine aqueous solution (650 g, concentration: 45% by weight) was mixed and neutralized with 461.2 g of orthophosphoric acid (concentration: 85%). To this solution was added a dispersion obtained by dispersing well 291.7 g of magnesium hydroxide in 1,000 ml of water, and these were mixed. The mixture was reacted, and heat-generated to form a white solid material. This white solid material was heated at 95° C. for 3 hours, and was then milled well with the addition of 3,000 ml of pure water. The solid material was filtered, washed with 3,000 ml of water, and then dried at 60° C. under reduced pressure to give 750 g of a white powder.

One gram of this white powder was added to 100 ml of each of pure water and the corresponding rumen solution, and the mixture was stirred. As a result, no apparent change in the form of the sample was observed in either case. This product was designated an intermediate composite salt III.

EXAMPLE 4

Intermediate composite salt of formula (4) [4]

A solution obtained by mixing and neutralizing 311 g of an L-lysine aqueous solution (concentration: 47% by weight) with phosphoric acid (concentration: 85%) was uniformly mixed with a dispersion obtained by dispersing well 291.7 g of magnesium hydroxide with 700 ml of water. Then, the mixed solution was reacted, and heat-generated to form a white solid material. This white solid material was heated at 90° C. for 3 hours, then milled, and dried at 60° C. under reduced pressure to obtain 750 g of a white powder.

One gram of this white powder was added to 100 ml of each of pure water and the corresponding rumen solution, and the mixture was stirred. As a result, no apparent change in the form of the sample was observed in either case. This product was designated an intermediate composite salt IV.

EXAMPLE 5

Intermediate composite salt of formula (4) [5]

Twenty grams of the white crystalline powder obtained in Example 1 were added to a solution obtained by mixing and neutralizing 4,386 g of an L-lysine aqueous solution (concentration: 20% by weight) with 231 g of phosphoric acid (concentration: 85%). Subsequently, a solution of 407 g of magnesium chloride 6-hydrate in 500 ml of water was gradually added thereto in small portions to form fine crystals. The resulting crystals were filtered, washed with 3 liters of water, and dried at 60° C. under reduced pressure to give 573 g of a white crystalline powder.

One gram of this white powder was added to 100 ml of each of pure water and the corresponding rumen solution, and the mixture was stirred. As a result, no apparent change in the form of the sample was observed in either case. This product was designated an intermediate composite salt V.

EXAMPLE 6

Intermediate composite salt of formula (4) [6]

Magnesium secondary phosphate 3-hydrate (87.2 g) was added to 730 g of an L-lysine aqueous solution (concentration: 40% by weight), and the mixture was heat-stirred at 80° C. for 3 hours. Consequently, particulate crystals of magnesium secondary phosphate disappeared, and fine crystals were formed. To this mixture were gradually added 46.1 g of phosphoric acid (concentration: 85%) and a solution of 98.6 g of magnesium sulfate 7-hydrate in 150 ml of water at a time. Then, the mixture became a viscous crystalline slurry. The resulting crystals were filtered, washed with 1,300 ml of water, and dried at 60° C. under reduced pressure to give 198 g of a white crystalline powder.

One gram of this white powder was added to 100 ml of each of pure water and the corresponding rumen solution, and the mixture was stirred. As a result, no apparent change in the form of the sample was observed in either case. This product was designated an intermediate composite salt VI.

EXAMPLE 7

Intermediate composite salt of formula (4) [7]

A solution of 610 g of magnesium chloride 6-hydrate in 1 liter of water was added at a time to a solution obtained by mixing and neutralizing 4,873 g of an L-lysine aqueous solution (concentration: 30% by weight) with 461 g of phosphoric acid (concentration: 85%). The resulting viscous mixture was uniformly mixed with a dispersion obtained by dispersing well 93.3 g of magnesium hydroxide in 700 ml of water, and the solution was allowed to stand overnight to form a white precipitate. This precipitate was filtered, washed with 7,000 ml of water, and dried at 60° C. under reduced pressure to give 980 g of a white powder.

One gram of this white powder was added to 100 ml of each of pure water and the corresponding rumen solution, and the mixture was stirred. As a result, no apparent change in the form of the sample was observed in either case. This product was designated an intermediate composite salt VII.

EXAMPLE 8

Final composite salt of formula (1) [1]

Each (250 g) of the intermediate composite salts I and II obtained in Examples 1 and 2 was mixed with 40 g of calcium chloride 2-hydrate and 2,000 ml of water, and the mixture was stirred at room temperature for 2 hours. The solid material was separated from this mixture through filtration, and was then dried. Thus, 253 g of a desired final composite salt I and 241 g of a desired final composite salt II were obtained.

EXAMPLE 9

Final composite salt of formula (1) [2]

Each (250 g) of the intermediate composite salts III and IV obtained in Examples 3 and 4 was mixed with 20 g of calcium chloride and 2,000 ml of water, and the mixture was stirred at room temperature for 2 hours. The solid material was separated from this mixture through filtration, and was then dried. Thus 250 g of a desired final composite salt III and 248 g of a desired final composite salt IV were obtained.

EXAMPLE 10

Final composite salt of formula (1) [3]

Each (100 g) of the intermediate composite salts V and VI obtained in Examples 5 and 6 was mixed with 2,000 ml of water together with 20 g of zinc chloride, and the mixture was stirred at room temperature for 3 hours. The solid material was separated from this mixture through filtration, and was then dried. Thus, 103 g of a desired final composite salt V and 103 g of a desired final composite salt VI were obtained.

EXAMPLE 11
Final composite salt of formula (1) [4]

One hundred grams of the intermediate composite salt VII obtained in Example 7 were mixed with 1,000 ml of water, and 30 g of ammonium aluminum sulfate (burnt alum) were added thereto. The mixture was stirred at room temperature for 2 hours. The solid material was separated from this mixture through filtration, and was then dried to obtain 101 g of a desired final composite salt VII.

EXAMPLE 12

With respect to the intermediate composite salts I to VII obtained in Examples 1 to 7 and the final composite salts I to VII obtained in Examples 8 to 11, the lysine content, the Mg content, the phosphorus content and the content of the polyvalent metal other than Mg were analyzed, and the results are shown in Table 1. The lysine content was analyzed through liquid chromatography using a solution of a sample in dilute hydrochloric acid. The Mg content was measured through ICP (induction coupling plasma) emission spectral analysis. Further, the elution into pure water, the protection in a corresponding rumen solution, the protection in a corresponding rumen solution when administering a small amount of a sample, and the elution into a corresponding abomasum solution are also shown in Table 1.

From this Table 1, it becomes apparent that in comparison with the intermediate composite salt, the final composite salt obtained by treating this intermediate composite salt with the salt of the polyvalent metal other than Mg exhibits the increased protection in the rumen and the excellent elution in the abomasum, and it, therefore, exhibits the excellent solubility as a whole.

TABLE 1

| | \multicolumn{7}{c}{Analysis of amino-acid composite salt composition and properties thereof (unit: wt. %)} |
| --- | --- | --- | --- | --- | --- | --- | --- |
| | I | II | III | IV | V | VI | VII |
| Intermediate composite salt | | | | | | | |
| Lysine content | 51.1 | 20.0 | 18.5 | 19.5 | 50.4 | 36.5 | 29.8 |
| Mg content | 8.5 | 15.4 | 16.6 | 16.2 | 8.4 | 11.8 | 13.4 |
| Phosphorus content as $PO_4$ | 10.8 | 14.8 | 15.8 | 16.5 | 10.7 | 12.7 | 13.5 |
| | 33.1 | 45.4 | 48.5 | 50.6 | 32.8 | 39.0 | 41.4 |
| Elution into pure water | 84.2% | 13.0% | 35.0% | 48.7% | 85.2% | 55.3% | 38.5% |
| Protection in rumen | 10% | 85% | 55% | 42% | 9% | 40% | 57% |
| Protection in rumen in administering small amount | 5% | 65% | 35% | 26% | 4% | 20% | 38% |
| Elution into abomasum | 100% | 100% | 100% | 100% | 100% | 100% | 100% |
| Final composite salt | | | | | | | |
| Polyvalent metal salt | $CaCl_2$ | $CaCl_2$ | $Ca(OH)_2$ | $Ca(OH)_2$ | $ZnCl_2$ | $ZnCl_2$ | burnt alum |
| Lysine content | 46.6 | 18.2 | 17.2 | 18.3 | 45.4 | 30.5 | 28.2 |
| Mg content | 7.5 | 14.8 | 15.1 | 15.7 | 8.0 | 11.7 | 13.2 |
| Polyvalent metal other than Mg | Ca | Ca | Ca | Ca | Zn | Zn | Al |
| Content | 2.6 | 2.0 | 3.6 | 4.0 | 2.8 | 2.6 | 0.8 |
| Phosphorus content as $PO_4$ | 10.9 | 14.9 | 15.9 | 16.7 | 10.9 | 12.9 | 14.1 |
| | 33.4 | 45.7 | 48.7 | 51.2 | 33.4 | 39.6 | 43.2 |
| Elution into pure water | 65.3% | 8.0% | 35.0% | 48.7% | 68.3% | 35.4% | 18.5% |
| Protection in rumen | 30% | 90% | 55% | 42% | 28% | 54% | 75% |
| Protection in rumen in administering small amount | 28% | 85% | 53% | 40% | 26% | 51% | 72% |
| Elution into abomasum | 100% | 100% | 100% | 100% | 100% | 100% | 100% |

EXAMPLE 13
Final composite salt of formula (1) [5]

L-arginine (174.2 g) and 98.0 g of phosphoric acid (concentration: 85%) were dissolved in 300 ml of water, and the solution were mixed with a dispersion obtained by dispersing well 72.9 g of magnesium hydroxide in 200 ml of water. Then, the mixture was reacted, and heat-generated to obtain a white solid material [intermediate composite salt of formula (4)]. This white solid material was heated at 95° C. for 3 hours, and 1,000 ml of pure water was then added thereto. The mixture was milled well, and 10 g of calcium hydroxide were added thereto. The resulting mixture was stirred for 2 hours. The solid material was filtered, washed with 1,000 ml of water, and dried at 60° C. under reduced pressure to obtain 245 g of a white powder (final composite salt).

One gram of this white powder was added to 100 ml of each of pure water and the corresponding rumen solution, and the mixture was stirred. Consequently, no dissolution was observed in either case. One gram of this white powder was dissolved in 100 ml of dilute hydrochloric acid, and the concentration of arginine was measured. As a result, it was found to be 350 mg/dl, and the content of arginine was 35.0%. Further, 1.00 g of this white powder was mixed with 1,000 ml of pure water, and the mixture was sonicated for 5 minutes. The concentration of arginine in the supernatant was measured. It was found to be 50 mg/dl, and the elution into pure water was 14.3%. The protection of this white powder in the corresponding rumen solution and the elution of the same in the corresponding abomasum solution were evaluated. Consequently, the protection in the corresponding rumen solution was 17%, and the elution into the abomasum solution was 100%.

EXAMPLE 14
Ruminant feed additive (1)

Two-hundred grams of the final composite salt I obtained in Example 8 were mixed with 150 g of a hardened soybean oil. Then, the mixture was heat-extruded at 65° C. through a die having a bore diameter of 1 mm using a heat-extrusion machine, and was cut to a length of approximately 1 mm to form granules having a diameter of approximately 1 mm.

With respect to the resulting granules, the protection in the corresponding rumen solution and the elution into the corresponding abomasum solution were evaluated. Consequently, the protection in the corresponding rumen solution was 65%, and the elution into the corresponding abomasum solution was 95%.

EXAMPLE 15
Ruminant feed additive (2)

Two-hundred grams of the final composite salt III obtained in Example 9 were mixed with 15 g of a methionine powder, 40 g of calcium carbonate, 20 g of casein sodium and 4 g of starch sodium glycolate, and 70 ml of water were added thereto. The resulting mixture was kneaded, extruded using a disc pelletizer having a bore diameter of 2 mm, cut to a length of approximately 2 mm, and dried to form granules having a diameter of approximately 2 mm.

The thus-obtained granules were further cut into smaller granules having a diameter of approximately 0.5 mm. The five granules thereof were heat-extracted with dilute hydrochloric acid, and the amino-acid content was measured. As a result, no difference in the amino-acid content was observed among these smaller granules. With respect to the thus-obtained granules, the protection in the corresponding rumen solution and the elution into the corresponding abomasum solution were evaluated. Consequently, the protection of lysine in the corresponding rumen solution was 98%, and the protection of methionine in the corresponding rumen solution was 66%. The elutions of lysine and methionine into the corresponding abomasum solution were both 95%. Further, with respect to the smaller granules having the diameter of approximately 0.5 mm, the protection in the corresponding rumen solution and the elution into the corresponding abomasum solution were evaluated. Consequently, the protection of lysine in the corresponding rumen solution was 96%, and the protection of methionine in the corresponding rumen solution was 63%. The elutions of lysine and methionine into the corresponding abomasum solution were both 98%.

EXAMPLE 16
Intermediate composite salt of formula (4) [8]

A dispersion of 1.55 kg of an L-lysine aqueous solution (concentration: 50% by weight) and 0.86 kg of magnesium hydroxide in 3.2 liters of water was mixed with 2.99 kg of 37-% phosphoric acid. After the mixture was heat-stirred at 80° C. for 3 hours, 20 liters of water were added thereto. To the reaction mixture were added a dispersion of 17.9 kg of a 50-% L-lysine basic aqueous solution and 9.84 kg of magnesium hydroxide in 36.8 liters of water and 34 kg of 37-% phosphoric acid over a period of 90 minutes at the same time. During that time, the temperature of the reaction solution was maintained at from 69° to 72° C. Further, the pH was between 8.2 and 8.5. Then, out of 128 kg of the slurry, 53 kg thereof were subjected to shaking-separation. The resulting crystals were washed with 36 liters of water. The wet crystals were dried in an air stream of 80° C. to give 11.4 kg of dry Mg salt crystals (intermediate composite salt).

The contents of lysine, Mg and $PO_4$ in the crystals were 20.0%, 18.9% and 51.1% respectively. Further, the elutions into the corresponding rumen solution, pure water and the corresponding abomasum solution were 76% (protection 24%), 17% and 100% respectively.

EXAMPLE 17
Final composite salt of formula (2) [1]

Seven grams of triphosphoric acid were dissolved in 500 ml of water, and 40 g of the Mg salt obtained in Example 16 and 8.75 g of calcium hydroxide were added thereto in this order. The mixture was stirred at room temperature for 1 hour, and was then subjected to suction-filtration to separate crystals. The resulting wet crystals were dried at 65° C. under reduced pressure to give 42.0 g of crystals (final composite salt).

The contents of lysine, Mg, P and Ca in the crystals were 11.8%, 13.1%, 16.6% and 8.4% respectively, and the water content was 11.5%. Further, the elutions into the corresponding rumen solution, pure water and the corresponding abomasum solution were 5% (protection 95%), 2% and 100% respectively.

COMPARATIVE EXAMPLE 1

Example 17 was repeated except that triphosphoric acid was not used to obtain 41.2 g of dry crystals.

The elutions into the corresponding rumen solution, pure water and the corresponding abomasum solution were 66% (protection 34%), 7% and 100% respectively.

EXAMPLE 18
Final composite salt of formula (2) [2]

Example 17 was repeated except that the amount of triphosphoric acid was changed to 2.6 g and the amount of calcium hydroxide to 1.8 g respectively to obtain 38.6 g of dry crystals (final composite salt).

The contents of lysine, Mg, P and Ca in the crystals were 13.8%, 18.3%, 18.4% and 2.3% respectively, and the water content was 11.5%. Further, the elutions into the corresponding rumen solution, pure water and the corresponding abomasum solution were 56% (protection 44%), 3% and 100% respectively.

EXAMPLE 19
Final composite salt of formula (2) [3]

Example 17 was repeated except that the amount of triphosphoric acid was changed to 2.6 g and the amount of calcium hydroxide to 13.3 g respectively to obtain 47.7 g of dry crystals (final composite salt).

The contents of lysine, Mg, P and Ca in the crystals were 9.8%, 13.5%, 13.6% and 12.9% respectively, and the water content was 13.7%. Further, the elutions into the corresponding rumen solution, pure water and the corresponding abomasum solution were 20% (protection 88%), 3% and 100% respectively.

EXAMPLE 20
Final composite salt of formula (2) [3]

Example 17 was repeated except that the amount of triphosphoric acid was changed to 1.0 g and the amount of calcium hydroxide to 4.4 g respectively to obtain 23 g of dry crystals (final composite salt).

The content of lysine was 13.5. Further, the elutions into the corresponding rumen solution, pure water and the corresponding abomasum solution were 45% (protection 55), 2% and approximately 100% respectively.

EXAMPLE 21
Final composite salt of formula (2) [5]

Triphosphoric acid (47.1 g) was dissolved in 500 ml of water, and 63.4 g of calcium hydroxide were added thereto. The solution was stirred at room temperature for 1 hour. The resulting slurry was subjected to suction-filtration to separate crystals. The crystals separated were washed well with water. The wet crystals were dried to obtain 96.6 g of calcium tripolyphosphate. Example 17 was repeated except that 15.7 g of calcium tripolyphosphate were used instead of tripolyphosphoric acid and calcium hydroxide to give 49.5 g of crystals (final composite salt).

The elutions into the corresponding rumen solution, pure water and the corresponding abomasum solution were 31% (protection 69%), 2% and 100% respectively.

EXAMPLE 22
Final composite salt of formula (2) [6]

Three grams of sodium tripolyphosphate were dissolved in 450 ml of water. To this solution were added 45.0 g of the Mg salt obtained in Example 16 and 5.0 g of calcium hydroxide. The mixture was stirred at room temperature for 2 hours. The resulting reaction slurry was subjected to suction-filtration, and the crystals precipitated were washed with 200 ml of water. The wet crystals were dried to give 37.8 g of dry crystals (final composite salt).

The contents of lysine, Mg, P and Ca in the crystals were 14.3%, 16.1%, 15.6% and 5.1% respectively, and the water content was 9.7%. Further, the elutions into the corresponding rumen solution, pure water and the corresponding abomasum solution were 53% (protection 47%), 1% and 100% respectively.

EXAMPLE 23
Final composite salt of formula (2) [7]

Example 22 was repeated except that 3.0 g of sodium hexametaphosphate was used instead of sodium triphosphate to give 46.4 g of dry crystals (final composite salt).

The contents of lysine, Mg, P and Ca in the crystals were 13.7%, 16.1%, 16.1% and 5.1% respectively, and the water content was 10.8%. Further, the elutions into the corresponding rumen solution, pure water and the corresponding abomasum solution were 23% (protection 77%), 2% and 100% respectively.

EXAMPLE 24
Final composite salt of formula (2) [8]

Example 22 was repeated except that 3.0 g of metaphosphoric acid were used instead of sodium triphosphate to give 45.8 g of dry crystals (final composite salt).

The contents of lysine, Mg, P and Ca in the crystals were 13.8%, 16.0%, 16.4% and 5.1% respectively, and the water content was 10.8%. Further, the elutions into the corresponding rumen solution, pure water and the corresponding abomasum solution were 26% (protection 74%), 2% and 100% respectively.

EXAMPLE 25
Final composite salt of formula (2) [9]

The slurry (19.5 kg) obtained in Example 16 was charged into a 30-liter container, and was heat-stirred at 55° C. To this slurry were added a dispersion of 50.48 kg of a 50-% lysine aqueous solution and 27.72 kg of magnesium hydroxide in 155.5 liters of water and 42.22 kg of 85-% phosphoric acid at the same time over a period of 15 hours. During that time, the rates of addition of the dispersion containing lysine and magnesium hydroxide and of phosphoric acid were controlled so as to maintain the pH of the slurry at 8.3. The amount of the solution in the container was kept constant by withdrawing from the container the slurry in the amount which was the same as those of the dispersion and phosphoric acid added. A total of 265.8 kg of the slurry (intermediate composite salt) were withdrawn through this procedure.

The slurry (22.15 kg) was stirred at 55° C. To this slurry were added an aqueous solution of 0.9 kg of pyrophosphoric acid in 8.4 liters of water and a dispersion of 1.22 kg of calcium hydroxide in 8.1 liters of water at the same time over a period of 2 hours. During that time, the pH of the slurry was maintained at 9.3. The resulting slurry was subjected to shaking-separation, and the crystals separated were washed with 42 liters of water. The wet crystals obtained were dried in an air stream of 90° C. to give 6.86 kg of dry crystals (final composite salt).

The contents of lysine, Mg, P and Ca in the crystals were 11.0%, 13.4%, 16.1% and 7.8% respectively, and the water content was 9.2%. The mother wash liquid (60 liters) contained 1.05 kg of lysine. However, Mg, P and Ca were contained therein in trace amounts, and 99.9% thereof were contained in the crystals (final composite salt). Further, the elutions of the crystals into the corresponding rumen solution, pure water and the corresponding abomasum solution were 8% (protection 92%), 2% and 100% respectively.

EXAMPLE 26
Final composite salt of formula (2) [10]

The slurry (1.95 kg) obtained in Example 16 was charged into a 3-liter container, and was heat-stirred at 55° C. To this slurry were added a dispersion of 5.05 kg of a 50-% lysine aqueous solution and 2.77 kg of magnesium hydroxide in 15.6 liters of water and 4.22 kg of 85-% phosphoric acid at the same time over a period of 15 hours. During that time, the rates of addition of the dispersion containing lysine and magnesium hydroxide and of phosphoric acid were controlled so as to maintain the pH of the slurry at 8.3. The amount of the solution in the container was kept constant by withdrawing from the container the slurry in the amount which was the same as those of the dispersion and phosphoric acid added. A total of 26.6 kg of the slurry (intermediate composite salt) were withdrawn through this procedure.

The slurry (22.2 kg) was stirred at 55° C. To this slurry were added 9.5 kg of a 10-% phosphoric acid aqueous solution and a dispersion of 1.11 kg of calcium hydroxide in 8 liters of water at the same time over a period of 2 hours. During that time, the pH of the slurry was maintained at 9.3. The resulting slurry was subjected to shaking-separation, and the crystals separated were washed with 40 liters of water. The wet crystals obtained were dried in an air stream of 90° C. to give 6.84 kg of dry crystals (final composite salt).

The contents of lysine, Mg, P and Ca in the crystals were 11.0%, 13.4%, 16.2% and 7.8% respectively, and the water content was 9.1%. The mother wash liquid (60 liters) contained 1.05 kg of lysine. However, Mg, P and Ca were contained therein in trace amounts, and 99.9% thereof were contained in the crystals (final composite salt). Further, the elutions of the crystals into the corresponding rumen solution, pure water and the corresponding abomasum solution were 8% (protection 92%), 2% and 100% respectively.

EXAMPLE 27
Ruminant feed additive (3)

Two-hundred grams of the dry polyvalent metal final composite salt (final composite salt) obtained in Example 25 were kneaded with a 2-% carboxymethyl cellulose sodium salt aqueous solution. The mixture was then extruded using a disc pelletizer having a bore diameter of 1.5 mm, cut to a length of approximately 2 mm, and dried to form granules having a diameter of approximately 1.5 mm. The granules were further dried.

With respect to the thus-obtained granules, the protection in the corresponding rumen solution and the elution into the corresponding abomasum solution were evaluated. Consequently, the elution into the corresponding rumen solution was 3% (protection 97%), and the elution into the corresponding abomasum solution was 95%.

EXAMPLE 28
Ruminant feed additive (4)

Two-hundred grams of the dry polyvalent metal composite salt obtained in Example 25 were mixed with 15 g of a methionine powder, 40 g of calcium carbonate, 20 g of casein sodium and 4 g of starch sodium glycolate, and 80 ml of water were added thereto. The resulting mixture was kneaded, extruded using a disc pelletizer having a bore diameter of 1.5 mm, cut to a length of approximately 2 mm, and dried to form granules having a diameter of approximately 1.5 mm. The granules were dried.

With respect to the thus-obtained granules, the elution into the corresponding rumen solution and the elution into the corresponding abomasum solution were evaluated. Consequently, the elution of lysine into the corresponding rumen solution was 5% (protection 95%), and the elution thereof into the abomasum solution was 95%. The elutions of methionine into the corresponding rumen solution and the corresponding abomasum solution were 37% (protection 63%) and 98% respectively.

EXAMPLE 29
Final composite salt of formula (3) [1]

Seven grams of triphosphoric acid were dissolved in 500 ml of water, and 40 g of the Mg salt obtained in Example 16 and 6.0 g of calcium hydroxide were added thereto in this order. The mixture was stirred at room temperature for 1 hour, and was then subjected to suction-filtration to separate crystals. The resulting wet crystals were dried at 65° C. under reduced pressure to give 40.5 g of crystals (final composite salt).

INDUSTRIAL AVAILABILITY

In accordance with the present invention, a phosphoric acid-amino acid-polyvalent metal composite salt (final composite salt) which is insoluble in a neutral or alkaline aqueous solution and is soluble in an acidic aqueous solution can be formed by treating a composite salt (intermediate composite salt) of a basic amino acid, magnesium and phosphoric acid with a salt of a divalent or trivalent (polyvalent) metal salt other than magnesium or by treating the intermediate composite salt with the polyvalent metal salt and a condensed phosphoric acid component (alone) or the condensed phosphoric acid component and a phosphoric acid component (in combination).

This final composite salt contains a basic amino acid such as lysine or the like which is often lacking in a ruminant feed additive. It is, therefore, formed into a ruminant feed additive which is excellent in terms of the protection of the amino acid in a rumen and the elution thereof into an abomasum. This ruminant feed additive can be formed into uniform granules which are less influenced by destruction owing to chewing of a ruminant or mixing with other feed components. Thus, the granules can be formed into a ruminant feed additive composition which is excellent in terms of the protection of the basic amino acid in the rumen and the elution thereof into the abomasum in comparison with the prior art.

The present invention further provides a feed additive composition which enables a biologically active substance to be effectively absorbed into a ruminant. Thus, it is extremely important industrially.

We claim:

1. A novel phosphoric acid-amino acid-polyvalent metal composite salt represented by formula (1)

$$R_a Mg_b M_c H_d PO_4 \cdot nH_2O \qquad (1)$$

wherein

R represents a basic amino-acid hydrogen cation,

Mg represents magnesium,

M represents a polyvalent metal of m-valence other than magnesium in which m is 2 or 3, H represents hydrogen, a is between 0.05 and 1.0, b is between 0.85 and 1.43, c is between 0.02 and 0.6, d is between 0 and 0.3, a+b×2+c×m+d=3, and n is between 0 and 20.

2. The phosphoric acid-amino acid-polyvalent metal composite salt of claim 1, wherein in formula (1), the basic amino acid is at least one type selected from lysine and arginine.

3. The phosphoric acid-amino acid-polyvalent metal composite salt of claim 1, wherein in formula (1), the divalent or trivalent (polyvalent) metal other than magnesium is at least one type selected from calcium, aluminum, zinc and iron.

4. A process for producing the phosphoric acid-amino acid-polyvalent metal composite salt of claim 1, which comprises dispersing magnesium secondary phosphate in a basic amino-acid aqueous solution, then heating the dispersion, separating the resulting precipitate, then mixing the precipitate separated with a polyvalent-metal-salt solution, and separating the mixture to obtain the phosphoric acid-amino acid-polyvalent metal composite salt.

5. A process for producing the phosphoric acid-amino acid-polyvalent metal composite salt of claim 1, which comprises mixing a magnesium salt aqueous solution with phosphoric acid in a basic amino-acid aqueous solution, separating the resulting precipitate, then mixing the precipitate separated with a polyvalent-metal-salt solution, and separating the mixture to obtain the phosphoric acid-amino acid-polyvalent metal composite salt.

6. A process for producing the phosphoric acid-amino acid-polyvalent metal composite salt of claim 1, which comprises adding magnesium hydroxide and/or magnesium oxide to a primary phosphate aqueous solution of a basic amino acid, mixing them to form a precipitate, then mixing the precipitate separated with a polyvalent-metal-salt solution, and separating the mixture to obtain the phosphoric acid-amino acid-polyvalent metal composite salt.

7. A process for producing the phosphoric acid-amino acid-polyvalent metal composite salt of claim 1, which comprises mixing phosphoric acid, a basic amino-acid aqueous solution and magnesium hydroxide and/or magnesium oxide, then drying the mixture, mixing this dry product with a polyvalent-metal-salt solution, and separating the mixture to obtain the phosphoric acid-amino acid-polyvalent metal composite salt.

8. A process for producing the phosphoric acid-amino acid-polyvalent metal composite salt of claim 1, which comprises separating (a) a precipitate obtained by dispersing magnesium tertiary phosphate in a basic amino-acid aqueous solution, a precipitate obtained by mixing a magnesium salt aqueous solution with phosphoric acid in a basic amino-acid aqueous solution, or a precipitate obtained by mixing a primary phosphate aqueous solution of a basic amino acid with magnesium hydroxide and/or magnesium oxide, then mixing the precipitate (a) separated with phosphoric acid, a basic amino-acid aqueous solution and magnesium hydroxide and/or magnesium oxide, drying the mixture, thereafter forming this dry product (b) into an aqueous slurry, and gradually adding a phosphoric acid aqueous solution and a calcium hydroxide aqueous dispersion to this slurry at the same time while stirring the same to replace a part of magnesium contained in said precipitate or dry product with calcium.

9. A novel phosphoric acid-amino acid-polyvalent metal composite salt represented by formula (2)

  (2)

wherein

R represents a basic amino-acid hydrogen cation,

Mg represents magnesium,

M represents a polyvalent metal of q-valence other than magnesium in which q is 2 or 3, H represents hydrogen, a is between 0.05 and 0.4, b is between 0.90 and 1.47, c is between 0.01 and 1.4, d is between 0 and 0.3, a+2×b+q×c+d=m+3, m is 0<m<1.12, and n is between 0 and 10.

10. The phosphoric acid-amino acid-polyvalent metal composite salt of claim 9, wherein in formula (2), the basic amino acid is at least one type selected from lysine and arginine.

11. The phosphoric acid-amino acid-polyvalent metal composite salt of claim 9, wherein in formula (2), the divalent or trivalent (polyvalent) metal other than magnesium is at least one type selected from calcium, aluminum, zinc and iron.

12. A novel phosphoric acid-amino acid-polyvalent metal composite salt represented by formula (3)

  (3)

wherein

R represents a basic amino-acid hydrogen cation,

Mg represents magnesium,

Z represents a polyvalent metal of q-valence other than an alkaline-earth metal in which q is 2 or 3, H represents hydrogen, a is between 0.05 and 0.4, b is between 0.90 and 1.47, c is between 0.01 and 1.4, d is between 0 and 0.3, a+2×b+q×c+d=m+3, m is 0<m<1.12, and n is between 0 and 10.

13. The phosphoric acid-amino acid-polyvalent metal composite salt of claim 12, wherein in formula (3), the divalent or trivalent (polyvalent) metal other than an alkaline-earth metal is at least one type selected from aluminum, zinc and iron.

14. A process for producing the phosphoric acid-amino acid-polyvalent metal composite salt of formula (2), which comprises bringing a phosphoric acid-amino acid-polyvalent metal composite salt (intermediate composite salt) represented by formula (4)

  (4)

wherein

R represents a basic amino-acid hydrogen cation,

Mg represents magnesium,

H represents hydrogen, a is between 0.05 and 1.0, b is between 1.0 and 1.47, c is between 0 and 0.3, a+2×b+c=3, and n is between 0 and 10 into contact with a condensed phosphoric acid component (alone) or the condensed phosphoric acid component and a phosphoric acid component (in combination) and a substance of a divalent or trivalent (polyvalent) metal other than magnesium.

15. The process of claim 14, wherein the condensed phosphoric acid component to be brought into contact with the phosphoric acid-amino acid-magnesium composite salt of formula (4) is at least one type selected from pyrophosphoric acid, tripolyphosphoric acid, tetrapolyphosphoric acid, trimetaphosphoric acid, tetrametaphosphoric acid, hexametaphosphoric acid and salts thereof.

16. The process of claim 14, wherein the substance of the divalent or trivalent (polyvalent) metal other than magnesium to be brought into contact with the phosphoric acid-amino acid magnesium composite salt of formula (4) is at least one type selected from halides, sulfates, nitrates, hydroxides and oxides of calcium, aluminum, iron and zinc.

17. The process of claim 14, wherein the amounts of the condensed phosphoric acid and phosphoric acid components and the substance of the divalent or trivalent (polyvalent)

metal other than magnesium are both between 0.004 and 1.2 mols per mol of phosphoric acid of the phosphoric acid-amino acid-magnesium composite salt of formula (4).

18. A ruminant feed additive composition, which contains as an active ingredient the phosphoric acid-amino acid-polyvalent metal composite salt of claim 1 which is insoluble in neutral or alkaline water and is soluble in acidic water, and which takes the form of a powder or granules.

19. The ruminant feed additive composition of claim 18, which further contains, in addition to said phosphoric acid-amino acid-polyvalent metal composite salt, another biologically active substance.

20. A ruminant feed additive composition, which contains as an active ingredient the phosphoric acid-amino acid-polyvalent metal composite salt of claim 9 which is insoluble in neutral or alkaline water and is soluble in acidic water, and which takes the form of a powder or granules.

21. A ruminant feed additive composition, which contains as an active ingredient the phosphoric acid-amino acid-polyvalent metal composite salt of claim 12 which is insoluble in neutral or alkaline water and is soluble in acidic water, and which takes the form of a powder or granules.

* * * * *